US009699447B2

(12) United States Patent
Bajema et al.

(10) Patent No.: US 9,699,447 B2
(45) Date of Patent: Jul. 4, 2017

(54) CALIBRATION OF A DYNAMIC DIGITAL IMAGING SYSTEM FOR DETECTING DEFECTS IN PRODUCTION STREAM

(71) Applicant: Frito-Lay North America, Inc., Plano, TX (US)

(72) Inventors: Rick Wendell Bajema, Plano, TX (US); Wilfred Marcellien Bourg, Jr., Melissa, TX (US); Scott Fagan, Dallas, TX (US); Sonchai Lange, Plano, TX (US); Kerwin Bradley, Boise, ID (US); David Ray Warren, Plano, TX (US)

( * ) Notice: Subject to any disclaimer, the term of this patent is extended or adjusted under 35 U.S.C. 154(b) by 673 days.

(21) Appl. No.: 13/803,484

(22) Filed: Mar. 14, 2013

(65) Prior Publication Data

US 2014/0146164 A1 May 29, 2014

Related U.S. Application Data

(60) Provisional application No. 61/729,883, filed on Nov. 26, 2012.

(51) Int. Cl.
| | | |
|---|---|---|
| H04N 17/00 | (2006.01) | |
| G01N 21/93 | (2006.01) | |
| B07C 5/342 | (2006.01) | |
| G01J 3/52 | (2006.01) | |

(52) U.S. Cl.
CPC .......... *H04N 17/002* (2013.01); *B07C 5/3422* (2013.01); *G01J 3/524* (2013.01); *G01N 21/93* (2013.01)

(58) Field of Classification Search
CPC .................. G01S 11/12; G06T 7/0075; G06T 2207/30261; H04N 13/02; G08G 1/165; G08G 1/168; G08G 1/16
USPC .......................................................... 348/47
See application file for complete search history.

(56) References Cited

U.S. PATENT DOCUMENTS

| | | |
|---|---|---|
| 3,840,931 A | 10/1974 | Bivens |
| 4,259,020 A | 3/1981 | Babb |
| 4,454,029 A | 6/1984 | Codding |
| 4,807,163 A | 2/1989 | Gibbons |
| 5,335,293 A | 8/1994 | Vannelli et al. |

(Continued)

FOREIGN PATENT DOCUMENTS

| | | |
|---|---|---|
| EP | 1166061 | 5/2003 |
| JP | 2004125675 A | 4/2004 |

(Continued)

OTHER PUBLICATIONS

MunsellStore.com, printed Mar. 21, 2013 and located at http://www.munsellstore.com/(X(1)S(5opipr45zxr54x555whmys21)/Default.aspx?gclid=CNOYj-id8LMCFQHNOgodBgkAlg&AspxAutoDetectCookieSupport=1.
PCT/US13/71498 Search Report and Written Opinion mailed May 12, 2014, 8 pages.
Pedreschi et al., "Quality Evaluation and Control of Potato Chips and French Fries" In: Da-Wen Sun: "Computer Vision Technology for Food Quality Evaluation", 2007 Elsevier, pp. 549-570.

(Continued)

*Primary Examiner* — Nguyen Truong
(74) *Attorney, Agent, or Firm* — Brandon V. Zuniga; Colin P. Cahoon; Carstens & Cahoon, LLP (57) ABSTRACT

A system and method for calibrating a dynamic digital imaging system for the detection of defects in a moving product stream. The system has an elevated platform above a conveying unit for receiving a reference color tile. The elevated platform allows for the passage of products to be inspected on the below conveying unit surface such that calibration and re-calibration processes during image capturing may be accomplished on a continuous basis without interruption of the product stream.

25 Claims, 8 Drawing Sheets

(56) References Cited

U.S. PATENT DOCUMENTS

| | | | |
|---|---|---|---|
| 5,533,628 | A | 7/1996 | Tao |
| 5,818,953 | A | 10/1998 | Queisser et al. |
| 5,850,472 | A | 12/1998 | Alston |
| 5,887,702 | A | 3/1999 | Mott |
| 5,944,598 | A | 8/1999 | Tong et al. |
| 5,991,046 | A | 11/1999 | Shakespeare |
| 6,011,540 | A | 1/2000 | Berlin et al. |
| 6,198,834 | B1 | 3/2001 | Belk et al. |
| 6,763,132 | B2 | 7/2004 | Freifeld |
| 7,068,817 | B2 | 6/2006 | Bourg, Jr. et al. |
| 8,139,896 | B1 | 3/2012 | Ahiska et al. |
| 2001/0048765 | A1 | 12/2001 | Yi et al. |
| 2002/0159643 | A1* | 10/2002 | DeYong ................. G06K 9/00 382/228 |
| 2004/0181302 | A1 | 9/2004 | Schrader |
| 2007/0153277 | A1 | 7/2007 | Shakespeare et al. |
| 2008/0283449 | A1 | 11/2008 | Madsen |
| 2009/0056872 | A1 | 3/2009 | Grove |
| 2009/0245616 | A1 | 10/2009 | De La Ballina et al. |
| 2010/0315068 | A1* | 12/2010 | Bentley ................. G01V 13/00 324/202 |
| 2011/0050880 | A1 | 3/2011 | Bourg, Jr. et al. |

FOREIGN PATENT DOCUMENTS

| | | |
|---|---|---|
| JP | 2010054342 A | 3/2010 |
| WO | 94/28397 | 12/1994 |

OTHER PUBLICATIONS

TOMRA Sorting Solutions | Food, Odenberg BEST, Odenberg Sentinel Optical Sorting, 4 pages.

Tomra Sorting Solutions | Food, Odenberg BEST, Odenberg Titan II Optical Sorting, 4 pages.

Abdullah et al., "Quality Inspection of Bakery Products Using a Color-Based Machine Vision System" Journal of Food Quality 23 (2000) pp. 39-50.

Brosnan et al., "Improving Quality Inspection of Food Products by Computer Vision—A Review" Journal of Food Engineering 61 (2004) pp. 3-16.

Davidson et al., "Fuzzy Models to Predict Consumer Ratings for Biscuits Based on Digital Image Features" IEEE Transactions on Fuzzy Systems, vol. 9, No. 1, Feb. 2001, pp. 62-67.

Pedreschi et al., "Grading of Potato Chips According to Their Sensory Quality Determined by Color" Food Bioprocess Technol, Mar. 30, 2011, 8 pages.

Key Technology, "Understanding How Electronic Sorting Technology Helps Maximize Food Safety" Published Jun. 2010, 7 pages.

Lu et al., "Evaluation of Pork Color by Using Computer Vision" Meat Science 56 (2000) pp. 57-60.

Tao et al., "Machine Vision for Color Inspection of Potatoes and Apples" American Society of Agricultural Engineers vol. 38(5) (1995) pp. 1555-1561.

Genius, optical sorter, printed Nov. 26, 2012 and located at http://www.bestsorting.com/sorting-food/sorters/genius-optical-sorter/.

PCT Search Report for PCT/US2013/071490 dated Apr. 18, 2014, 2 pages.

* cited by examiner

CALIBRATION OF A DYNAMIC DIGITAL IMAGING SYSTEM FOR DETECTING DEFECTS IN PRODUCTION STREAM

TECHNICAL FIELD

The present invention relates in general to digital image analysis, and more particularly to calibration of a dynamic digital imaging system for detecting anomalies or defects in digital images of continuously moving production streams.

BACKGROUND

Use of image analysis in detection of anomalies or defects has been in use in various fields. Specifically, the food processing industry has incorporated digital image analysis in conjunction with continuous conveyors in automated food sorting systems. For example, some prior art methods provide for the inspection of food products and other products or items whose quality can be visually ascertained. As with any advanced imaging or spectral analysis, the detected images need to be compared against a reference, meaning that the system needs to be calibrated to ensure consistent measurements. Yet the systems and methods known in the art of image analysis often require calibration procedures that interrupt the capturing of images for defect detection. This can be problematic when the defect detection system is in use in conjunction with continuous production lines (e.g., continuous conveyor systems transporting products to be inspected for defect).

Therefore, a need exists for a system and method that provides for calibration and recalibration of a digital defect detection system, that does not require slowing down or stopping the production conveyor system. Further, an improved digital defect detection system needs to be capable of retrofitting an existing product conveyor system. Finally, a need exists for the digital defect detection system and method that provide accurate and real-time calibration of the image acquisition and analysis systems during continuous production.

SUMMARY

In accordance with one aspect of the present invention, a method for calibrating a dynamic digital imaging system for detecting defects in a production stream is provided that substantially eliminates or reduces disadvantages associated with previous methods of static calibration. The method, in one embodiment, includes the steps of (a) placing a calibration color tile on a platform elevated above the conveyor in the field of view of a camera; (b) obtaining light absorption data of the calibration color; (c) calculating a component color intensity of the light absorption data of the calibration color; (d) normalizing the component color intensities of the calibration color; (e) removing the platform out of the field of view of the camera; (f) obtaining light absorption data of the products; (g) calculating a component color intensity of the light absorption data of the products; (h) normalizing the component color intensities of the products; and (i) calculating a quality index score of the products based on the component color intensities of the calibration color and the products.

In accordance with another aspect of the present invention, a system for calibrating a dynamic digital imaging system for detecting defects in production stream is disclosed. In some embodiments, the system includes a conveyor unit having a first frame extending along at least a portion of a width of the conveyor unit; a platform elevated above the conveyor unit on at least one support movably coupled to a track within the first frame; and a slot within the platform for receiving a color tile comprising a plurality of reference color segments. Some embodiments also include a second frame coupled to the first frame directly across the width of the conveyor unit; an imaging unit comprising a camera having a field of view, a camera window, and a control/data line; and/or a control unit comprising a processor, a memory, and a display device wherein further the imaging unit is in communication with the control unit through the control/data line.

Certain embodiments of the present invention may provide a number of technical advantages. For example, according to one embodiment of the present invention, the digital imaging system can be calibrated substantially simultaneously as the subjects move along a conveyor system. Yet another technical advantage associated with one embodiment of the present invention is its versatility. The features provided by the present invention may be applied to any conveyor systems for production of materials that require quality assurance. While the embodiments described herein use the example of food product conveyor system, the systems and methods in this disclosure are easily adaptable to any continuous production context. Without being limiting, some examples of the type of industry and application of the disclosed method and system include: baked confectionary goods, savory snack food, candies (e.g., jelly beans, chocolates, candy coated chocolates, taffy, and colored gummy snacks), wood products, paper products, textiles, and many more.

Certain embodiments of the present invention may enjoy some or all of these advantages. Other technical advantages may be readily apparent to one skilled in the art from the following figures, description, and claims.

BRIEF DESCRIPTION

For a more complete understanding of the present invention and its advantages, reference is made to the following description, and the accompanying drawings, in which.

DETAILED DESCRIPTION

Figure 1:
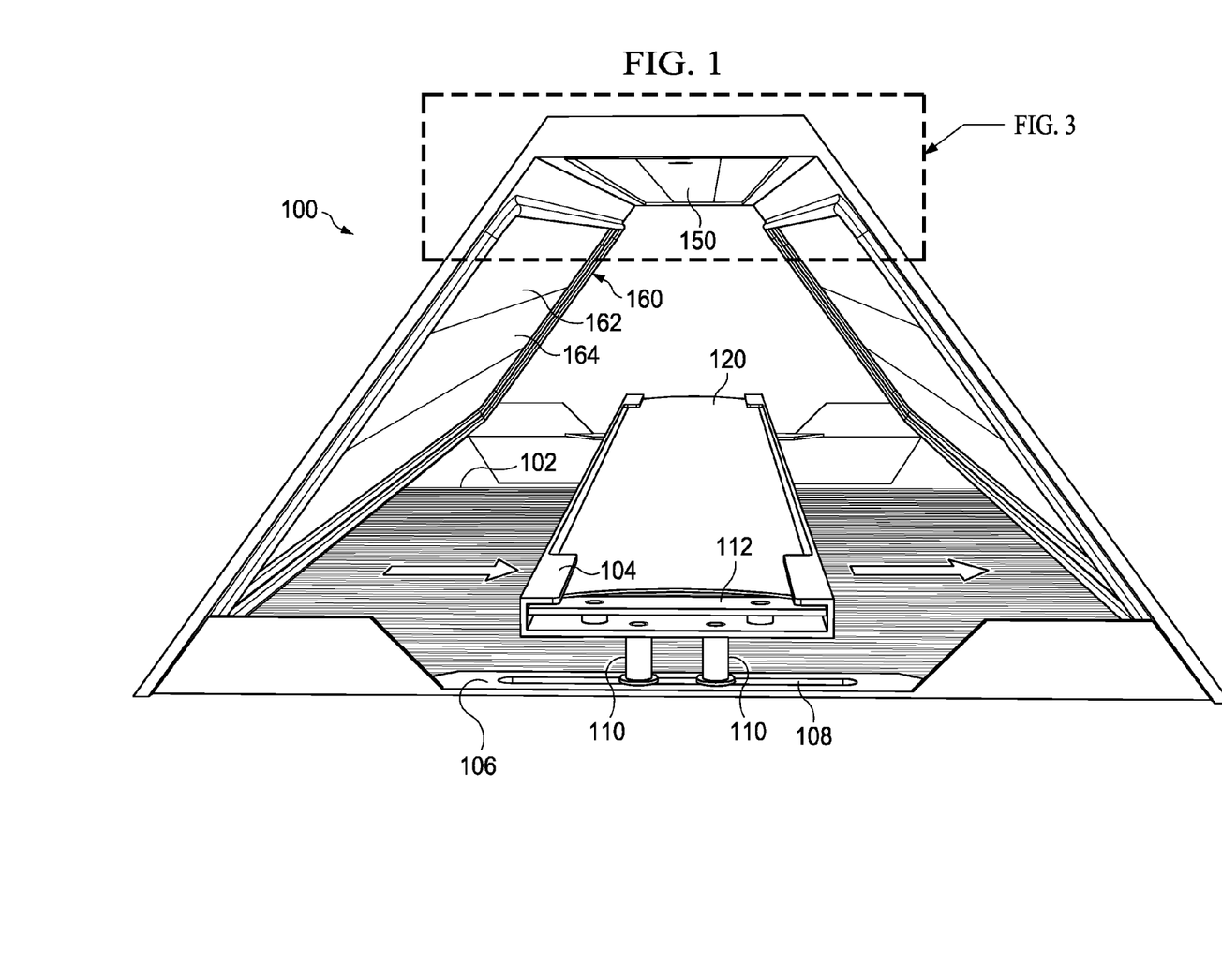
FIG. 1 illustrates a perspective view of a system for calibrating a dynamic digital imaging system for detecting defects in production stream according to a particular embodiment.

FIG. 1 illustrates a dynamic digital imaging system for detecting defects in production stream according to some embodiments. As used herein, the term "dynamic digital imaging system" refers to any system operable to obtain digital image of continuously moving subjects (e.g., continuously moving production stream). System 100 includes a control unit, a conveyor unit, a calibration reference unit, a lighting unit, and an imaging unit. Each unit is described in further detail below.

In at least one embodiment, the control unit is a computer having a processor, a memory, a display device (e.g., a monitor), and an input device (e.g., keyboard, mouse, or touchpad). In some embodiments, the control unit is also equipped with a network interface and is connected to a network. Such embodiment provides an advantage of the ability to control the system 100 at a remote location. In some embodiments, the control unit controls the conveyor unit, the calibration reference unit, the lighting unit 160, and the imaging unit. In other embodiments, the conveyor unit is controlled separately by an operator or another system. As will be discussed in further detail below, the calibration reference unit may also be manually controlled by an operator. In some embodiments, the lighting unit 160 and the imaging unit are controlled by separate systems in communication with each other. Still in another embodiment, an operator manually adjusts the light source 162 intensity based on the data from the captured image. In an alternative embodiment, the lighting unit 160 is a static unit, and the control unit adjusts the light intensity data by applying a scaling factor.

In some embodiments, the conveyor unit is a conveyor belt 102. In other embodiments, the conveyor unit is any system capable of supporting and transporting a continuous stream of products. In some embodiments, the imaging, lighting, and reference color units are housed in a portable enclosure (as shown in FIG. 1) that can be moved away from conveyor belt 102 to another location along the production stream. This portable enclosure provides an advantage of easily retrofitting an existing conveyor system.

In one embodiment as shown in FIG. 1, the calibration reference unit comprises a platform 104, a frame 106, a track 108, support posts 110, a slot 112 along the platform 104, and one or more color tiles 120. It should be noted that while the embodiment of FIG. 1 depicts two support posts 110, in one embodiment, the calibration reference unit comprises only one support post 110. Thus, generally, the calibration reference unit comprises at least one support post 110. In one embodiment, shown more closely in FIG. 2, the platform 104 is supported by frame 106 having a track 108 in which the support posts 110 are free to slide. In such embodiment, the calibration reference unit may move in a direction perpendicular or parallel to the movement of the conveyor belt 102. This may allow the calibration reference unit to be moved into or out of the field of view of the imaging unit as needed. For example, when the system 100 is not in a calibration sequence, the support posts 110 of calibration reference unit slide along the track 108 out of the field of view of the imaging unit in the direction parallel to the movement of the conveyor belt so that the imaging unit can capture images of the product stream on the conveyor belt 102. Conversely, when the system 100 is in calibration or recalibration mode, the calibration reference unit slides into the field of view of the imaging unit. In some embodiments, the operator of the system 100 manually moves the calibration reference unit into or out of the field of view, whereas in other embodiments the control unit automatically moves it depending on whether the system 100 is in a calibration mode or detection mode. While FIG. 1 illustrates simple support posts 110 sliding along the track 108, any mechanism capable of moving calibration reference unit in and out of the field of view of the imaging unit can be substituted. Some examples include rollers, casters, wheels, magnetic tracks, or more sophisticated robotic controls.

Generally, the platform 104 may comprise a definable height such that it is raised above the conveyor belt 102 with one or more support posts 110 or suitable substitute thereof. The height of the support posts 110 can be adjusted, for example, according to the size and shape of the products being transported on the conveyor belt 102. In one embodiment, the support posts 110 are tall enough to provide at least about a three-inch (about 7 or 8 cm) clearance between the conveyor belt 102 surface and the bottom of the platform 104. This can be advantageous in that calibration of the system 100 can occur without interrupting the continuous flow of the product stream.

The platform 104 has a slot 112 in which one or more color tiles 120 can slide and be supported. The color tiles 120 can be a single tile of one color, a single tile with multiple colors, or multiple tiles of various colors. The color tiles 120 are made of any suitable material, including paper, polymer (including ultra-high molecular weight polyethylene, acrylonitrile butadiene styrene (ABS), polyoxymethylene, nylon, polytetrafluoroethylene, etc.), metal, ceramic, composite, or wood. The size of the color tiles 120 may also vary depending on the needs of the imaging unit. In one embodiment, the color tile 120 comprises the same width as the width of the conveyor belt 102, and is disposed perpendicular to the flow of the product stream on the conveyor belt 102. In the particular embodiment shown in FIG. 1, the color tile 120 is about 48 inches (about 122 cm) wide and between about 6 to about 8 inches (about 15 to about 20 cm) long. In one embodiment, when sliding a color tile perpendicularly to the direction of conveyor belt travel, a color tile may be relatively small because the individual pixel size is on the order of 0.023 inch square. To prevent interference with light reflected from surrounding areas, smaller color tile is preferred in one embodiment. Another advantage of using smaller color tiles is the flexibility to use smaller and lighter weight support mechanisms. In some embodiments, the size range of the color tile ranges from about 0.1 inch to about 0.25 inch square. It should be noted that with smaller tiles, the support mechanism should be virtually "invisible" to the imaging unit as it has opportunity to influence local lighting in the region of the tile. In another embodiment, a color tile 120 of a narrower width runs parallel to the direction of the conveyor belt 102. In one embodiment, a color tile 120 may slide perpendicular to the direction of the conveyor belt. In another embodiment, a color tile 120 may further slide parallel to the direction of the conveyor. In some embodiments, the color tile is capable of both perpendicular and parallel movements relative to the direction of product flow on the conveyor belt. In some embodiments, color tiles 120 may comprise a matte finish, thereby avoiding the presence of a glare surrounding the light source or lighting when its surface is illuminated. Alternatively, in one embodiment, the lighting source may comprise a reflective strip or reflector 164 along the length of the calibration reference unit.

The lighting unit 160 (best depicted in FIG. 1) includes a light source 162 and optionally includes a reflector 164. The light source 162 may be any suitable source of light capable of sufficiently illuminating the reference calibration unit and the product stream on the conveyor unit 102. Some examples of suitable light source include incandescence (e.g., conventional incandescence bulb or a halogen lamp), electroluminescence (e.g., light emitting diodes (LEDs)), fluorescence (e.g., compact fluorescent lamps or a plasma lamp), high-intensity discharge lamp, arc lamp, etc. In one embodiment, the lighting unit 160 is affixed on the side walls of the system 100 enclosure as shown in FIG. 1. The walls are angled in one embodiment as depicted in the figures so as to not cast a shadow or a glare on the imaging subject during image capturing. Because the product stream on the conveyor 102 and the calibration reference unit are at a different height relative to the light source, a fixed lighting unit may cast a shadow or glare at one height but not the other. The reflector 164 alleviates any shadow or glare issue by redirecting the light. The reflector 164 is any suitable device capable of reflecting light, such as a mirror or a metal surface. The reflector 164 surface need not be polished as it is sufficient that it be opaque and reflective of "white" light in some embodiments. In other embodiments, e.g., where a specific color measurement is being made, a reflector 164 that selectively absorbs undesirable light wavelengths is used. In other embodiments where fluorescence is measured, the reflector 164 might take one wavelength of light and transpose it to a preferred wavelength that would then be detectable. For the foregoing examples, color tiles 120 of specific properties that would mimic the feature being measured may be needed. The color tiles 120 as well as the reflector 164 could be designed and fabricated, for example, by using semiconductor-like techniques known in the art for doping a substrate with chemicals that exhibit desirable properties.

In some embodiments, both or either the reflector 164 and the whole lighting unit 160 are actuated by the control unit. It should be noted that the height difference between the conveyor belt 102 and the calibration reference unit also poses an issue of light intensity difference. The light source 162 being generally above the subject to be illuminated, the calibration reference unit receives higher intensity of light than the product stream below the unit on the conveyor belt 102. Thus, in some embodiments, the control unit adjusts the output intensity of the light source 162 depending on whether the system 100 is in calibration mode or detection mode. In other embodiments, the lighting intensity is calculated and corrected based on the relationship between the intensity and the distance from the emitting source. Such relationship can be determined theoretically or empirically and then integrated into the calibration algorithm.

Figure 3:
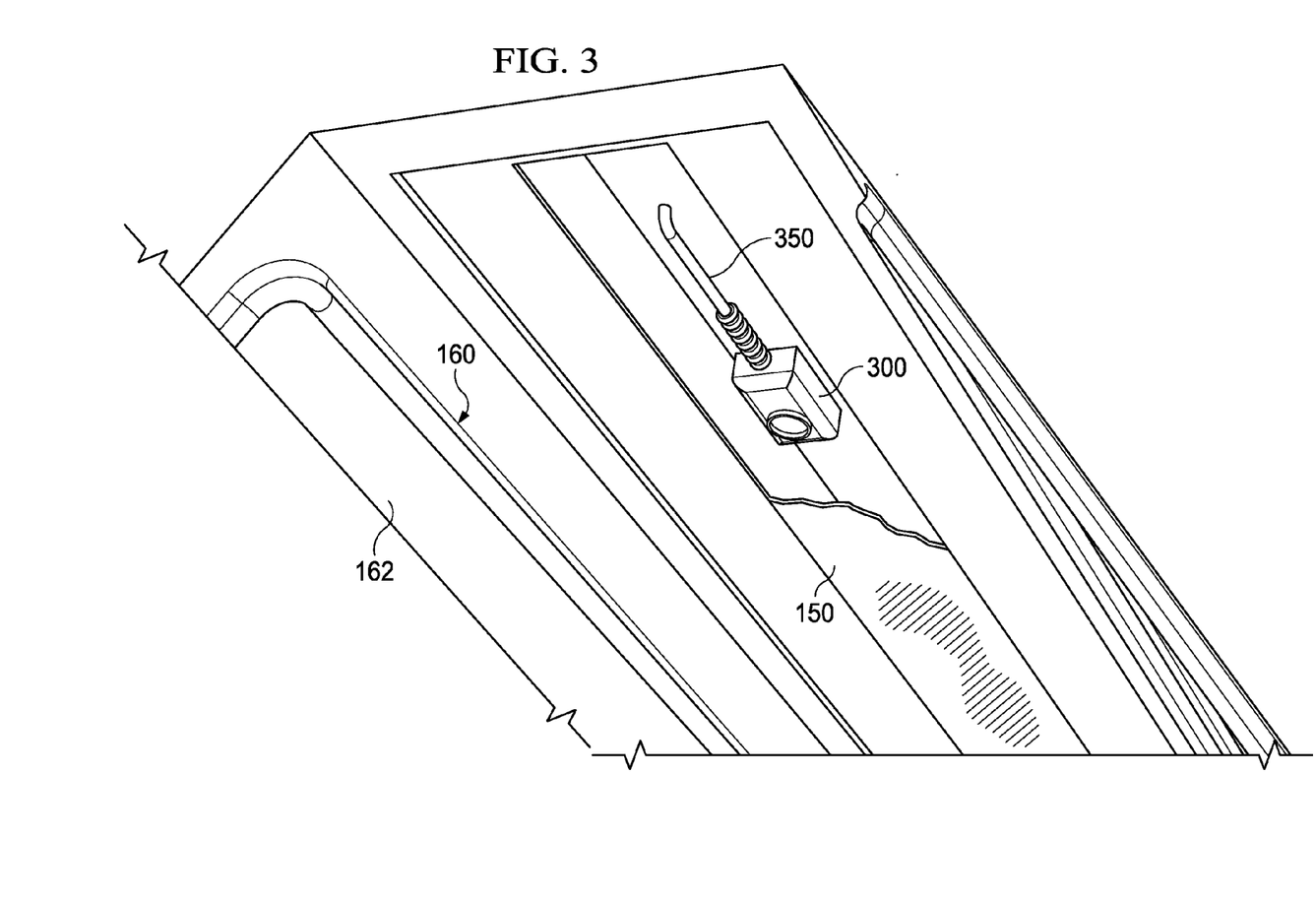
FIG. 3 illustrates a perspective view of a system for calibrating a dynamic digital imaging system for detecting defects in production stream according to a particular embodiment.

FIG. 3 illustrates a close-up of one embodiment of the imaging unit. The imaging unit includes a camera window 150, a line scan camera 300, and a control/data line 350 in some embodiments. In other embodiments, the line scan camera 300 is substituted with any device capable of capturing color images of the product flow and the calibration reference unit. The imaging unit is situated generally above the imaging subject (e.g., conveyor belt 102 and the calibration reference unit). The camera window 150 is made of any optically transparent material capable of transmitting light without or with minimal loss due to absorption by the camera window 150 (e.g., glass or polymer). One of the purposes of the camera window 150 is to protect the line scan camera 300 and the control/data line 350 from the surrounding environment of the production line (e.g., dust particles) and to enable efficient cleaning.

Figure 2:
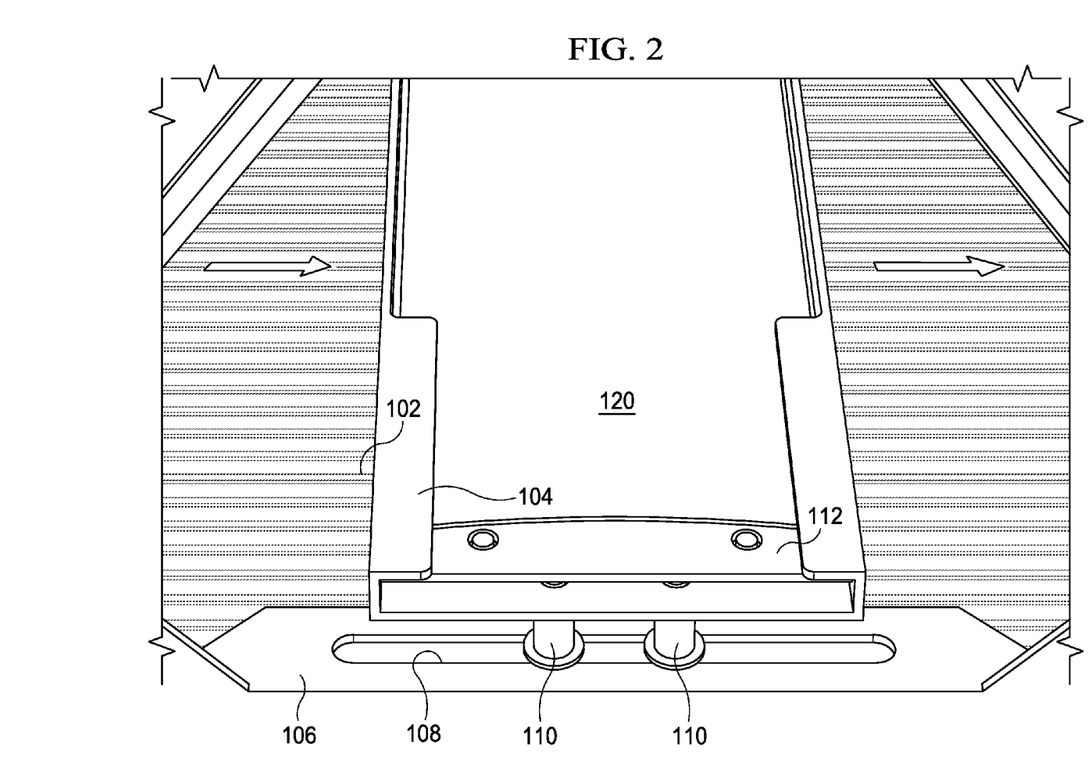
FIG. 2 illustrates a perspective view of a system for calibrating a dynamic digital imaging system for detecting defects in production stream according to a particular embodiment.

In the particular embodiment shown in FIGS. 1 through 3, the camera window 150 extends across the width of the conveyor belt 102. In such embodiment, the line scan camera 300 moves across the camera window 350, and thereby captures a line image (i.e., a linear array of pixels) of the subject. The line scan camera 300 oscillates across the camera window 350 in a generally continuous manner to generate a two-dimensional image (i.e., aggregation of linear arrays of pixels). In other embodiments, the line scan camera 300 does not oscillate but rather is a linear array of adjacent sensor elements that sample the individual pixel. In one embodiment, 2,048 individual sensor elements are linearly arranged and simultaneously samples pixels 0 through 2047, respectively. This can be continuously repeated to create a continuous two-dimensional image. Such two-dimensional image can be divided into essentially four square frames of 1024×1024 pixels each for analysis in one embodiment. The size of the frames is not limited to any particular dimension, and may be adjusted according to the needs of the system. For example, in some embodiments, the frame can be as small as 2048×1 pixels or as large as limitation of the memory employed in the control unit, e.g., 2048×100,000 pixels. The image data acquired by the line scan camera 300 is transmitted through the data/control line 350 to the control unit. The data/control line 350 also actuates the movement of the line scan camera 300. In one embodiment, the line scan camera 300 samples all 2048 pixels at the rate of about 4000 times per second. This sampling rate allows for essentially a square frame at an underlying conveyor speed of about 600 feet per minute. In embodiments where a different image capturing device is used, the movement of the camera may be obviated if the camera has sufficiently wide field of view to capture the image across the entire width of the conveyor belt 102 (e.g., wide-angle camera or a video camera). In some embodiments, the line scan camera 300 is equipped with one or more light sensors, such as charge-coupled device (CCD), reverse-biased light emitting diodes (LEDs), photodiodes, complementary metal-oxide-semiconductors (CMOS), video camera tubes (e.g., vidicon), or any other suitable image capturing device that can digitize an image and input into a digital array format inside the processor of the control unit.

Figure 4:
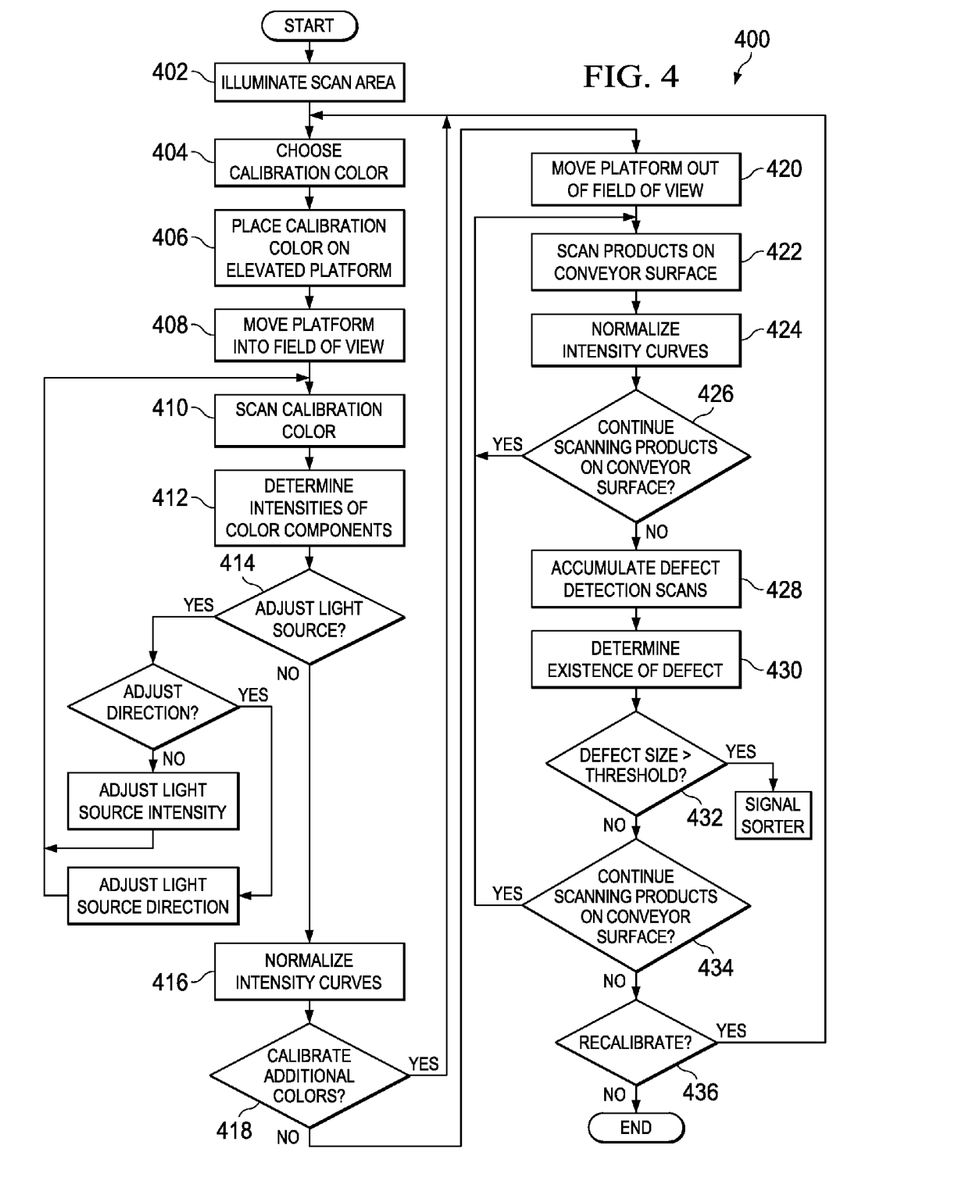
FIG. 4 illustrates a flow chart of a method for calibrating a dynamic digital imaging system for detecting defects in production stream according to a particular embodiment.

FIG. 4 illustrates one embodiment of the method 400 of the system 100 in operation. Method 400 illustrates one embodiment of the calibration mode and the detection mode sequence. As used herein, the term "calibration" means the process that includes acquiring light absorption data of one or more preselected reference color, normalizing the light absorption data, and producing a set of finalized light absorption data against which the detection scan data would be referenced and compared. It should be noted that the term normalization is not interchangeable with calibration as both the calibration data set and the detection scan data set are normalized in some embodiments. As will be further explained below (in description accompanying FIGS. 5A and 5B), normalization is generally a mathematical process in which a set of data is multiplied by a factor to reduce it to a simpler form to aid in comparison of one data set to another. In embodiments where several reference colors are scanned, the calibration process includes acquiring the light absorption data for each reference color, normalizing each set of data, and accumulating a finalized data set against which the detection scan data would be referenced and compared. Even in an embodiment where only one reference color is used, the term "calibration" is not interchangeable with "normalization" in the sense that the calibration process may also include adjustment of light source 162 (as discussed below). In embodiments where the light source 162 is adjusted from the calibration scan to the detection scan to account for the difference in light intensity at the elevated level, the term "calibration" may also encompass multiplying by a scaling factor accordingly. In other words, "normalization" generally means mathematical manipulation of one or more sets of light absorption data based on a scaling factor derived internally from that data set, whereas "calibration" generally means the entire process by which the finalized reference color light absorption data set is obtained. Referring to the embodiment depicted in FIG. 4, the calibration mode generally includes steps 404 to 420 (and step 436 for recalibration) and the detection mode includes steps 422 to 434 (with one or more steps being optional as described further below). The normalization process can be conceptualized as adjusting the gain of each of the individual pixels of the sensor such that they respond the same way to the illumination field. For example, light at the edges of the illumination field is less intense due to the fact that there are no sources of illumination beyond the edge of the field of view (e.g., the conveyor belt). This is seen, for example, in FIGS. 5A and 5B, which illustrate the "left" side of a line scan in one embodiment (e.g., pixels 0 through 1023 of the 2048×1 pixels frame). The intensity level starts off quite a bit lower at pixel 0 and gradually increases, but it plateaus and levels off from about pixel 512 to pixel 1023. The "right" side scan (e.g., pixels 1024 through 2047) would similarly show a fairly level intensity from pixel 1024 to about pixel 1536, and would gradually decrease in intensity as it approaches the right edge of the scan. This is referred to as a "bread loaf" effect, because the line scan looks like the top of a bread loaf. The act of normalizing addresses this phenomenon by adjusting the gain on the camera signal generated from the edge region to raise the signal level and flatten the response. A similar effect may occur within the field of view when not all the light sources 162 give off precisely the same amount of energy or even the same spectral content. Normalization in this context, then, is the act of making each pixel of the imaging device have a similar—though not precisely the same—color response to a given stimulus. The normalization target has slightly different spectral response across its width and length, so, while normalization is an attempt to account for systematic error in the way the camera records illumination, it is only as good as the consistency of the normalization target. In one embodiment, the normalization target is a uniform color sheet of formica that is glued to a metal backing plate. Calibration, on the other hand, involves passing known colors (e.g., Munsell color tiles) through the illumination field and adjusting a color correction table to make sure that the color observed is equal to the standardized color of that tile. By introducing tiles of many colors (colors that represent the overall range of interest for the given machine) known as a gamut, it is possible to assure that, for a given color presented to the camera within the illumination field the, image will be reproduced within a degree of precision consistent with limits imposed by the variability of each step in this process.

The following paragraphs describe use of the system 100 in the context of potato chip quality assurance inspection. But it should be noted that the following description is only one example of the many variations made possible by the alternative embodiments of the system 100 as described in preceding paragraphs. System 100 is capable of use in any field or industry where it is desirable to inspect quality of the products by digital image analysis—e.g., where the appearance (color, shape, or size) of the finished product is a factor—including but not limited to food processing, consumer goods, fashion, or automobile.

Returning to the method depicted in FIG. 4, the method 400 begins at step 402 where the scan area (i.e., imaging subject) is illuminated by activating the lighting unit 160. At step 404, system 100 select a color tile 120 of a certain calibration color among a predetermined or preselected set of colors. The calibration color can be any wavelength/frequency within the visible range of the electromagnetic spectrum. In one embodiment, the system 100 is equipped with a plurality of color tiles 120 ranging in numbers from two to as many as several thousands. While having a larger range of colors better enables the system 100 to calibrate the full spectrum, the operator (or the system) may choose or preselect few colors that are of high interest in the context. The reference color tiles 120 can be preselected according to the specific needs of products being inspected or to cover the full color spectrum.

At step 406, the chosen color tile 120 is placed on an elevated platform 104. The color tile 120 is placed on the elevated platform 104 by sliding into or engaging the slot 112. The elevated platform 104 is moved into the field of view at step 408 via the control unit or manually by an operator. At step 410, the line scan camera 300 captures a scan of the calibration color tile 120 and sends it to the control unit, which receives the scan data and stores it to memory. At step 412, the processor of the control unit determines the intensity and the color components of the light absorbed by the sensors in the line scan camera 300.

Figure 5A:
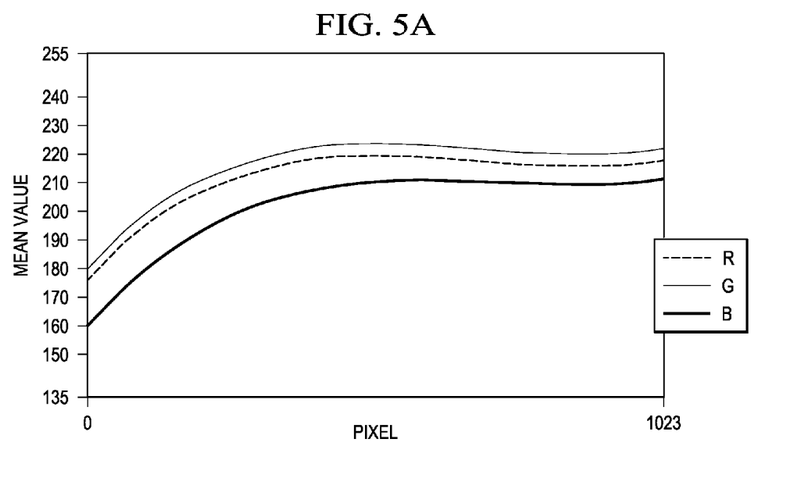
FIGS. 5A and 5B illustrate exemplar line scans of calibration reference unit at the conveyor belt height and at an elevated height, respectively, according to one embodiment.
Figure 5B:
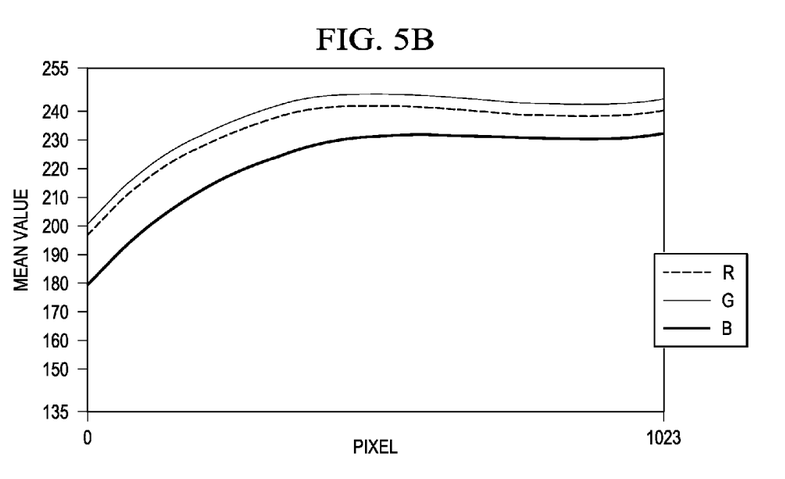

As illustrated in FIGS. 5A and 5B, the line scan data can be visualized as a two-dimensional plot with the pixel number (the location along the linear array of pixels) on the x-axis and the light intensity level on the y-axis. The line scan data can be further broken down into the intensity levels of individual color components—such as the red, green, blue (RGB) components—at each pixel. As previously mentioned, a problem can arise when the calibration reference unit is elevated above the conveyor belt 102 because the intensity of light absorbed or reflected at each level can differ even if the same subject is scanned. For example, FIG. 5A illustrates the color component intensity analysis of a scan of a gray color tile 120 at the conveyor belt 102 level; FIG. 5B illustrates the same at the elevated platform 104 level. It is readily apparent that the intensity levels FIG. 5B is much higher than that of FIG. 5A, almost to the point of saturating the light sensors and topping out. This can cause errors when comparing the calibration data to the scans of the product flow.

Thus, returning to the general method depicted in FIG. 4, in one embodiment, after the control unit determines intensities of the color components, the system 100 decides at step 414 whether to adjust the light source 162. One adjustment is to increase or decrease the light source 162 intensity. In one embodiment, the control unit processor automatically adjusts the light source 162 intensity if the measured intensity is above or below a predetermined threshold. In another embodiment, the control unit processor sends an alert (e.g., via the display device) to the operator of the system 100 to adjust the light source 162 manually. Still in other embodiments, the operator of the system 100 adjusts the light source 162 intensity based on the scan observations without a prompt to do so from the control unit. Step 414 further includes adjusting the light source 162 direction in some embodiments. As seen in FIGS. 5A and 5B, the intensity curves have much lower value at the beginning of the scan (near pixel 0) and then level off as the scan continues. This result may occur due to shadow or glare on subject surface (in this case, the gray color tile 120 or due to the bread loaf effect discussed above). In some embodiments, the control unit adjusts the angle or direction of the light source 162, whereas the operator of the system 100 does so manually in other embodiments. After adjusting the light source 162—whether by adjusting the intensity, direction, or both—the method 400 cycles back to step 410 to obtain a new calibration line scan. It should be noted that step 414 is optional and that the method can proceed from step 412 directly to the normalization step 416 in some embodiments. Indeed, the shape of any particular intensity curve may not be material after the normalization step.

Figure 6A:
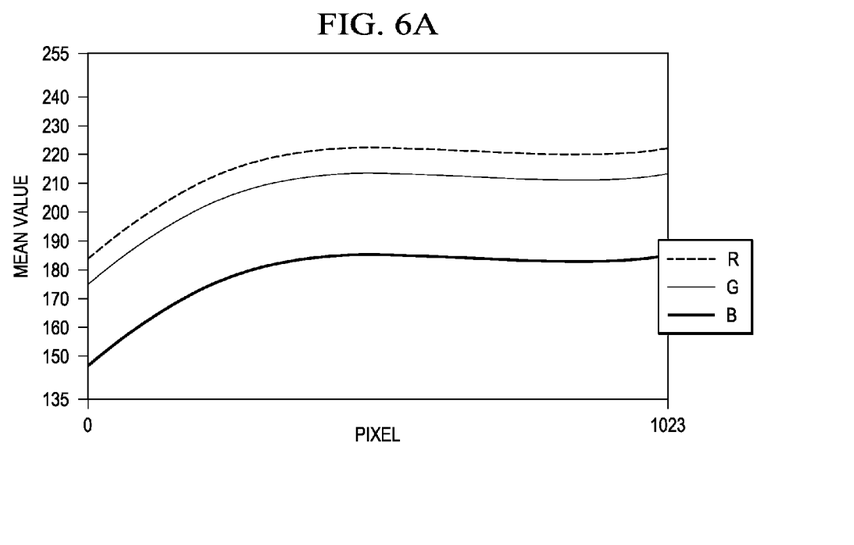
FIGS. 6A and 6B illustrate exemplar line scan raw data and the normalized plot, respectively, according to one embodiment.
Figure 6B:
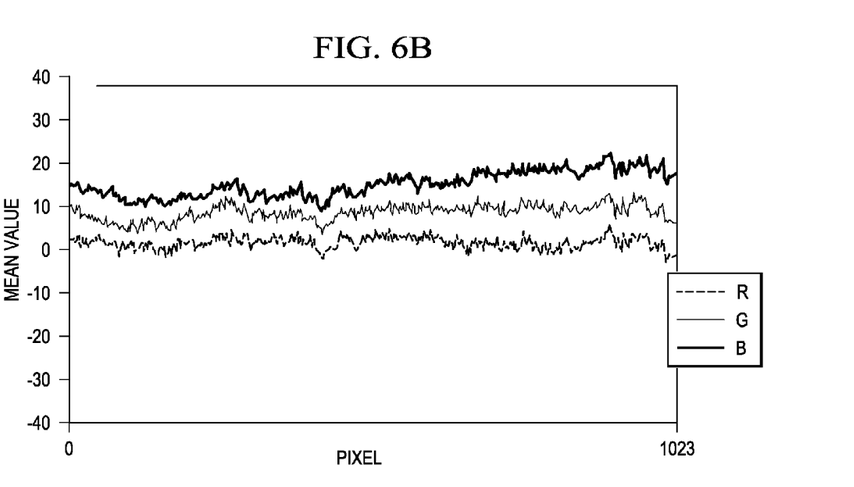

Following the optional adjustment of the light source at step 414 in FIG. 4, at step 416, the processor of the control unit normalizes the color component intensity curves. As illustrated in FIGS. 6A and 6B, the raw data from a calibration scan (FIG. 6A) is multiplied by a scaling factor (for example, $y_{max}$ of the RGB curves) to yield a set of normalized curves (FIG. 6B) for a more effective comparison. The normalized RGB curves are substantially linear, which makes it easier to compare the relative intensities among the R, G, and B components. Furthermore, the normalized plot can more easily be thought of as the imaging subject's absorption plot (inverse of the reflected light intensity data acquired by the imaging unit). A more linear curve provided by the normalization step 416 facilitates easier detection of defects when compared to the product flow scans.

After normalization, at step 418, system 100 optionally decides whether additional colors should be calibrated. If more colors are to be calibrated, method 400 cycles back to step 404. If sufficient number of colors has been calibrated, the method 400 proceeds to the next step. At step 420, system 100 moves the elevated platform 104 (either via the control unit or by the operator) out of the field of view of the line scan camera 300. Because the calibration sequence (e.g., steps 404 through 420) for each color is as short as a fraction of a second, calibration and recalibration can occur without having to interrupt the production flow. The processing time to validate or calibrate the colors can take up to about a minute, but the operation of the system is not effected during that time. The continuous production flow need not stop during calibration if the conveyor belt 102 is not moving at such a rapid pace so as to advance a so high volume of products during the calibration mode that it would affect quality control.

Upon exiting the calibration mode, system 100 proceeds to the defect detection mode. At step 422, the imaging unit captures a line scan of the product on the conveyor belt 102 surface. As with the calibration scan, the acquired data is transmitted to the control unit through the control/data line 350, and stored in the control unit memory. At step 424, the control unit processor normalizes the color component intensities of the defect detection scans. The control unit processor then decides whether to continue scanning the products on the conveyor belt 102 surface at step 426. If determined in the affirmative at step 426, steps 422 and 424 are repeated. If determined in the negative, the processor accumulates the defect detection scans stored in the memory at step 428. In some embodiments, system 100 continually repeats steps 422 through 426 while simultaneously transmitting the earlier acquired data to the control memory unit.

At step 430, the processor determines whether a defect exists among the accumulated scan data. The defect determination step 430 is automated, in one embodiment, based on an algorithm comprising various factors, including the color, shape, or size of the defect. Not all potentially defective pixels are treated the same. Instead, each cluster or group of potentially defective pixels are assigned a quality index score. In some embodiments, the algorithm includes a set of threshold levels of quality index score for each type of defect. For example, a set of 300 orange pixels on a given potato chip may be deemed as defective as a set of 10 black pixels. Thus, a black defect may have a threshold level of 15 maximum pixels whereas an orange defect may have a threshold of 500 pixels. This is different than some prior art quality control methods where the presence of any single defect (or a pixel representing a defect) would be treated the same. The threshold values are chosen according to the needs of a particular application. The algorithm is stored in the control unit memory, and the processor calls upon the stored algorithm at step 432 to determine whether the defect size is above the relevant threshold. If so, system 100 sends a signal to the sorter to sort out the potentially defective product for further inspection. If not, method 400 proceeds to next steps. At step 434, system 100 determines whether to continue scanning the product stream on the conveyor belt 102 surface. If determined in the affirmative, the method 400 cycles back to step 422 and the detection mode continues.

It should be noted that the data from the imaging unit can be influenced by subtle changes in settings or conditions. For example, even though the line scan camera 300 is focused on the calibration color tile 120, if the surrounding area, such as the conveyor belt 102, changes color, the line scan result changes. For example, the conveyor belt 102 after an extended use of transporting potato chips can become orange to brown color. Some of the light emitted from the light source 162 is absorbed by the conveyor belt 102. Thus, when the calibration scan of a color tile 120 is taken against the backdrop of a clean conveyor belt 102 (as illustrated in FIG. 5B) is compared to one that is taken against a used, brown conveyor belt 102 (as illustrated in FIG. 6A), the blue intensity curve is noticeably lower in FIG. 6A. Thus, as the conveyor belt 102 ages and changes color, system 100 may need recalibration. At step 436, the processor determines whether recalibration is needed. If determined in the affirmative, the method 400 cycles back to step 404. If determined in the negative, the method 400 proceeds to subsequent steps.

While method 400 has been above described in one embodiment, there are many possible embodiments and variations on the method of using system 100. For example, as noted above, the adjustment of the light source 162 at step 414 can be an optional step. The recalibration step 436 can occur after the initial defect detection scan at step 422 or between any subsequent detection scans; the recalibration step 436 need not come after step 432. Furthermore, the detection scan data need not be normalized at step 424 after each and every scan. The normalization 424 of the defect detection scans can occur after all of the detection data are accumulated at step 428. One of ordinary skill in the art can appreciate that many of the steps in method 400 can be reordered, made optional, or occur substantially simultaneously without going beyond the scope of this disclosure.

Figure 7:
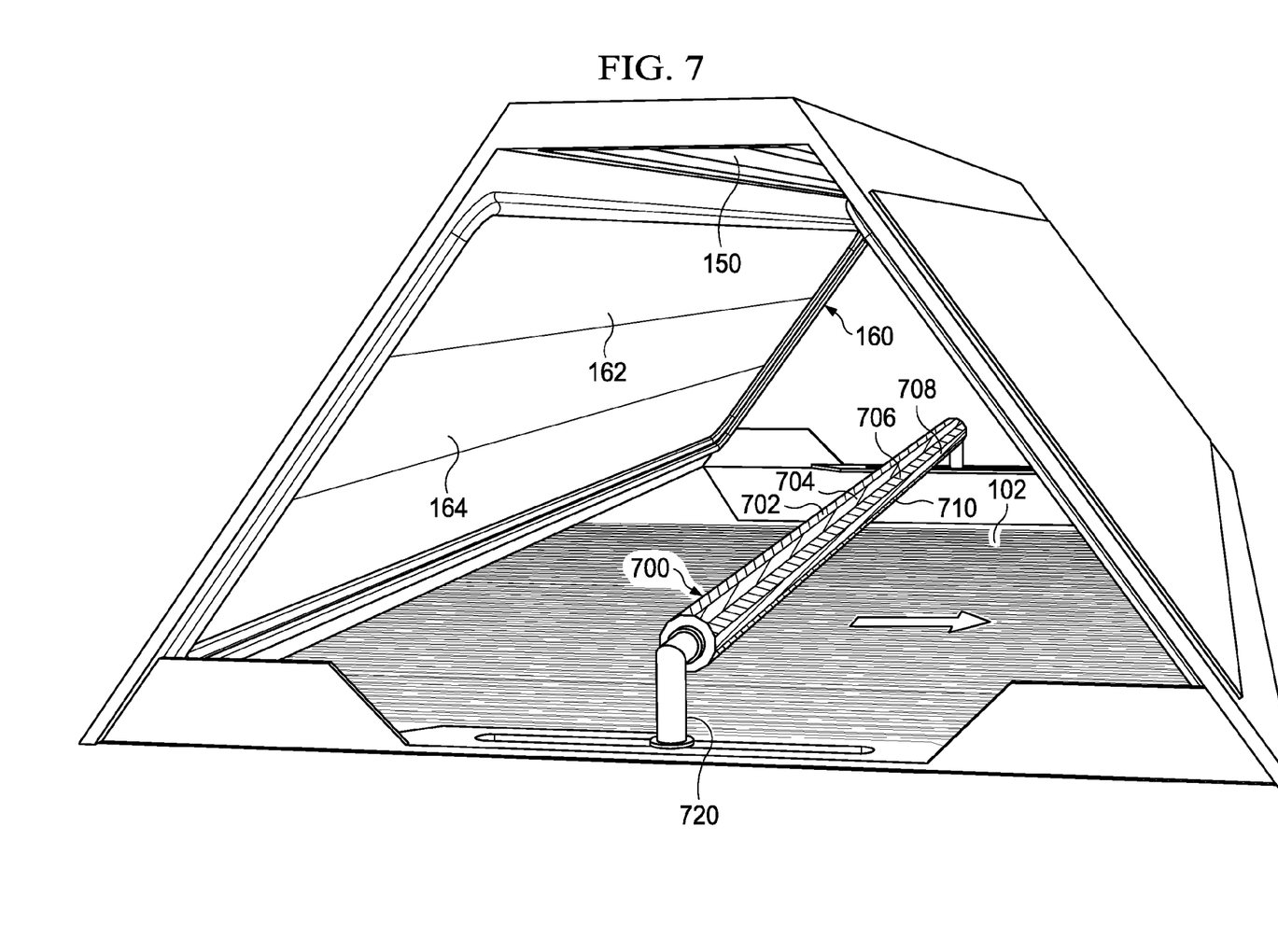
FIG. 7 illustrates a perspective view of a system for calibrating a dynamic digital imaging system for detecting defects in production stream according to an alternative embodiment.

Furthermore, the system 100 may also be varied. Specifically, the calibration reference unit need not comprise a color strip 120. For example, as illustrated in FIG. 7, the reference colors are arranged on a spinning roller 700 in one embodiment. The spinning roller 700 has a plurality of color segments 702, 704, 706, 708, 710, which may be chosen according to the specific needs of an inspection process. In one embodiment, the roller 700 rests on a set of support posts 750 on either end of the roller 700. In one embodiment, the control unit rotates the spinning roller 700 sufficient to place the next color segment in the field of view of the camera. The axis of rotation is through the center of the cylinder of the roller in one embodiment. But the color segments need not be a horizontal strip along the length of the spinning roller 700 as shown in FIG. 7. In another embodiment (not shown), the color segments are arranged in a diagonal manner so that the spinning roller 700 may continuously rotate as the imaging unit continuously captures calibration scans of various colors.

Figure 8:
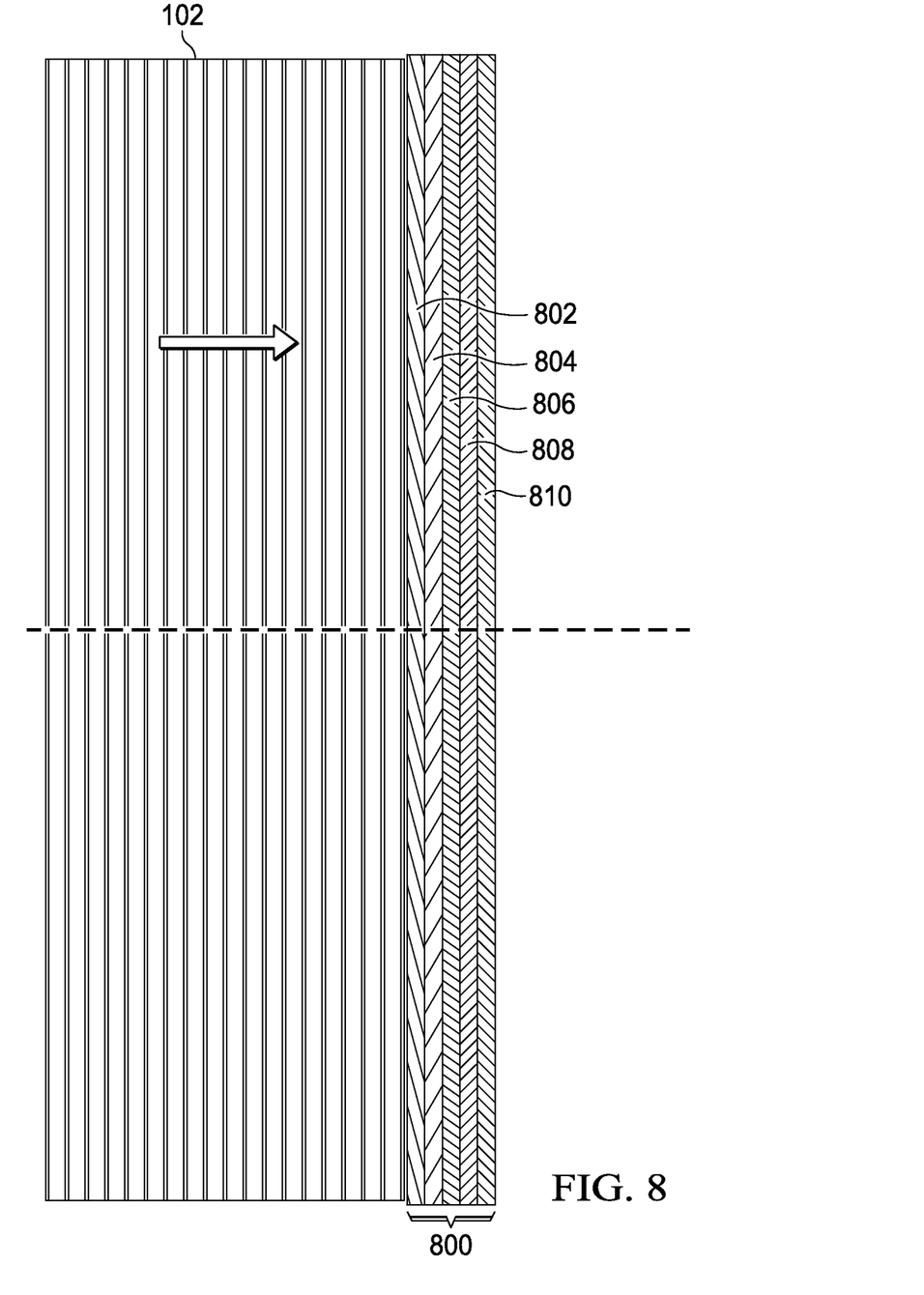
FIG. 8 illustrates a top view of a system for calibrating a dynamic digital imaging system for detecting defects in production stream according to an alternative embodiment.

In yet another embodiment, the color tiles 120 are affixed parallel to the direction of advancement of the conveyor belt 102 as illustrated in FIG. 8. The parallel color strip 800 comprises a plurality of color segments 802, 804, 806. 808, 810 running parallel to the direction of the conveyor belt 102 in some embodiments. As the line scan camera travels along the path shown in dotted line, it captures both a product stream defect detection scan on the conveyor belt 102 as well as a calibration scan of the reference color strip 800. Thus, each defect detection scan can be calibrated against the reference. In some embodiments, there is a barrier separating the conveyor belt 102 and the parallel color strip 800 within the system 100 enclosure to prevent any dust or waste accumulation on the parallel color strip 800. The parallel color strip 800 need not run the entire length of the conveyor belt 102, but can be long enough to cover the field of view of the imaging unit in some embodiments. A person having ordinary skill in the art would appreciate that in the embodiments where the parallel color strip 800 is used, many of the steps in method 400 can be either eliminated or occur simultaneously.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the spirit and scope of the appended claims. Alternative embodiments that result from combining, integrating, or omitting features of the embodiments are also within the scope of the disclosure.

In order to assist the United States Patent and Trademark Office (USPTO) and any readers of any patent issued on this application in interpreting the claims appended hereto, Applicants wish to note that the Applicants: (a) do not intend any of the appended claims to invoke paragraph six (6) of 35 U.S.C. section 112 as it exists on the date of the filing hereof unless the words "means for" or "step for" are specifically used in the particular claims; and (b) do not intend, by any statement in the specification, to limit this invention in any way that is not otherwise reflected in the appended claims.

What is claimed is:

1. A method of calibrating a dynamic digital imaging system for detecting defects in a production stream on a conveyor having a plurality of articles of products, wherein the method comprises:
    a) placing a calibration color tile having a calibration color on a platform elevated above the conveyor in a field of view of an imaging unit;
    b) obtaining light absorption data of the calibration color using the imaging unit;
    c) calculating a component color intensity of the light absorption data of the calibration color using a processor;
    d) normalizing the component color intensity of the calibration color;
    e) removing the platform out of the field of view of the imaging unit; and
    f) obtaining light absorption data of the articles using the imaging unit;
    wherein the method further comprises:
        transporting a continuous flow of the production stream on the conveyor, wherein the platform is elevated above the production stream; and
        performing steps a)-f) without interrupting the continuous flow of the product stream on the conveyor.

2. The method of claim 1 further comprising:
    g) calculating a component color intensity of the light absorption data of the articles using the processor;
    h) normalizing the component color intensity of the articles; and
    i) calculating a quality index score of the articles based on the component color intensity of the calibration color and the articles.

3. The method of claim 2 further comprising:
    j) recalling defect threshold data stored in a memory; and
    k) comparing the quality index score with the defect threshold data.

4. The method of claim 1, wherein the platform is removed out of the field of view of the imaging unit by moving in a direction parallel to a flow of the conveyor.

5. The method of claim 1, wherein the platform is removed out of the field of view of the imaging unit by moving in a direction perpendicular to a flow of the conveyor.

6. The method of claim 1 further comprising adjusting an output intensity of an illumination source.

7. The method of claim 6, wherein the output intensity of the illumination source is adjusted based on light absorption data of the calibration color.

8. The method of claim 6, wherein the output intensity of the illumination source is adjusted based on light absorption data of the articles.

9. The method of claim 1 further comprising adjusting a direction of an illumination source using a reflector.

10. The method of claim 9 wherein the direction of the illumination source is adjusted based on light absorption data of the calibration color.

11. The method of claim 1, wherein step d) comprises normalizing the component color intensity of the calibration color by adjusting the gain of each individual pixel of a sensor of the imagining unit.

12. The method of claim 2, wherein step d) comprises normalizing the component color intensity of the calibration color by adjusting the gain of each individual pixel of a sensor of the imagining unit.

13. The method of claim 2, wherein step d) comprises normalizing the component color intensity of the calibration color by adjusting the gain of each individual pixel of a sensor of the imagining unit; and
    wherein step h) comprises normalizing the component color intensity of the articles by adjusting the gain of each individual pixel of a sensor of the imagining unit.

14. A system for calibrating a dynamic digital imaging system for detecting defects in a production stream of products comprising:
    a conveyor unit having a first frame extending along at least a portion of a width of a conveyor unit;
    a platform elevated above the conveyor unit by a first support movably coupled to the first frame; and a reference color tile placed on the platform;

wherein the platform is configured to provide a clearance between the conveyor unit and the platform; and wherein the platform is configured so that, when the platform is used to calibrate the dynamic digital imaging system, the clearance is sufficiently large that the production stream can pass below the platform without interrupting a continuous flow of the production stream on the conveyor unit.

15. The system of claim 14 wherein the reference color tile comprises a plurality of reference color segments.

16. The system of claim 14 further comprising a second frame positioned directly across the width of the conveyor unit from the first frame, wherein the platform is further supported by a second support removably coupled to a track within the second frame.

17. The system of claim 14 wherein the platform is elevated at least 7 centimeters from an upper surface of the conveyor unit.

18. The system of claim 14 further comprising an imaging unit comprising a camera having a field of view, a camera window, and a control/data line.

19. The system of claim 18 wherein the camera is a linear array of light sensors.

20. The system of claim 14 further comprising a lighting unit comprising a light source and a reflector.

21. The system of claim 14 wherein the first support is movably coupled to a track within the first frame.

22. The system of claim 14 further comprising a control unit comprising a processor, a memory, and a display device wherein further an imaging unit is in communication with the control unit through a control/data line.

23. The system of claim 14 wherein the color tile is on a roller operable to rotate about its longitudinal axis.

24. The system of claim 21 wherein the support is a beam operable to move within the track.

25. The system of claim 14, further comprising:

a slot within the platform for receiving a reference color tile.

* * * * *

UNITED STATES PATENT AND TRADEMARK OFFICE
CERTIFICATE OF CORRECTION

PATENT NO. : 9,699,447 B2  
APPLICATION NO. : 13/803484  
DATED : July 4, 2017  
INVENTOR(S) : Rick Wendell Bajema et al.

It is certified that error appears in the above-identified patent and that said Letters Patent is hereby corrected as shown below:

In the Claims

In Claim 11, Column 12, at Line 49, please delete "imagining" and replace with -- imaging --.

In Claim 12, Column 12, at Line 53, please delete "imagining" and replace with -- imaging --.

In Claim 13, Column 12, at Line 57, please delete "imagining" and replace with -- imaging --.

In Claim 13, Column 12, at Line 60, please delete "imagining" and replace with -- imaging --.

In Claim 14, Column 12, at Line 65, please delete "a" and replace with -- the --.

Signed and Sealed this  
Ninth Day of October, 2018

Andrei Iancu  
*Director of the United States Patent and Trademark Office*